United States Patent [19]
Kendig et al.

[11] Patent Number: 5,945,594
[45] Date of Patent: Aug. 31, 1999

[54] METHOD AND APPARATUS FOR THE ELECTROCHEMICAL INSPECTION OF GALVANIZED CABLE AND METHOD AND APPARATUS FOR PREDICTING THE CORROSION LIFE OF GALVANIZED CABLE UNDERGOING MECHANICAL FATIGUE

[75] Inventors: Martin Kendig, Thousand Oaks; Andrew McKie; Michael Mitchell, both of Newbury Park, all of Calif.

[73] Assignee: Meritor Light Vehicle Systems-France, Troy, Mich.

[21] Appl. No.: 09/172,517

[22] Filed: Oct. 14, 1998

[51] Int. Cl.[6] .......................... G01N 17/02; G01N 3/32; G01N 27/26; G01R 27/08

[52] U.S. Cl. .................. 73/86; 204/404; 73/812; 324/700

[58] Field of Search .......................... 73/86, 812, 865.6, 73/158; 324/691–724; 204/404, 286

[56] References Cited

U.S. PATENT DOCUMENTS

| | | | |
|---|---|---|---|
| 3,890,567 | 6/1975 | Knufflmann et al. | 324/701 |
| 3,947,343 | 3/1976 | Delves-Broughton et al. | 204/286 |
| 4,403,499 | 9/1983 | Sack et al. | 73/158 |
| 4,806,849 | 2/1989 | Kihira et al. | 324/700 |
| 4,812,175 | 3/1989 | Reghi | 148/258 |
| 5,212,982 | 5/1993 | Macchiarulo et al. | 324/700 |
| 5,275,704 | 1/1994 | Yang | 204/153.11 |
| 5,294,265 | 3/1994 | Gray et al. | 148/250 |
| 5,433,834 | 7/1995 | Belz et al. | 204/213 |
| 5,481,198 | 1/1996 | Patel | 324/700 |
| 5,519,330 | 5/1996 | Yamauchi et al. | 324/700 |
| 5,755,948 | 5/1998 | Lazaro et al. | 205/143 |

OTHER PUBLICATIONS

Fürbeth et al., "Investigation of the Delamination of Polymer Films from Galvanized Steel with the Scanning Kelvinprobe," *Fresenius' Journal of Analytical Chemistry*, vol. 353, pp. 337–341 (1995).

Isaacs et al., "Determination of Surface Inhomogeneities Using a Scanning Probe Impedance Technique," *Corrosion*, vol. 36, No. 6, pp. 269–274 (Jun. 1980).

Isaacs et al., "Surface Scanning Techniques to Locate and Study Defects in Painted Zinc and Zinc Alloy Coated Steels," presented as Paper No. 393 at Corrosion/95, Mar. 1995, Orlando, FL.

Isaacs et al., "Measurements of corrosion at defects in painted zinc and zinc alloy coated steels using current density mapping," *Corrosion*, vol. 52, No. 3, pp. 163–168 (Mar. 1996).

*Primary Examiner*—Hezron Williams
*Assistant Examiner*—Chad Soliz
*Attorney, Agent, or Firm*—Suiter & Associates

[57] ABSTRACT

A method and apparatus for examining the electrochemical kinetics occurring at the surface of a galvanized steel cable undergoing fatigue in the presence of a corrosive environment allows the prediction of the corrosion life of the cable. In one embodiment, an apparatus for detecting localized corrosion in a cable is provided undergoing mechanical fatigue, comprising a weir cell containing an electrolyte and a reference electrode, one or more pulleys, and a motion control device. In other embodiments, methods for detecting and monitoring the electrochemical response of corrosion coupled to fatigue in a galvanized steel cable are provided wherein the potential between a reference electrode and a moveable cable under tension and undergoing fatigue are recorded and/or monitored. In further embodiments, a method and apparatus are provided for inspecting entire runs of cable for localized corrosion, zinc porosity, and corrosion inhibition efficiency. In still further embodiments, methods for the selective application of corrosion protectants to critical cable regions are provided which extend cable corrosion life.

24 Claims, 15 Drawing Sheets

METHOD AND APPARATUS FOR THE ELECTROCHEMICAL INSPECTION OF GALVANIZED CABLE AND METHOD AND APPARATUS FOR PREDICTING THE CORROSION LIFE OF GALVANIZED CABLE UNDERGOING MECHANICAL FATIGUE

FIELD OF THE INVENTION

The present invention relates generally to the corrosion of galvanized steel cable and, more particularly, to a method and apparatus for the prediction of cable life of a galvanized steel cable undergoing mechanical fatigue in a corrosive environment.

BACKGROUND OF THE INVENTION

Corrosion is a redox process by which metals are oxidized by oxygen in the presence of moisture. The corrosion of iron may be characterized by the half-reaction:

$$Fe \rightarrow Fe^{2+} + 2e^-.$$

The two electrons so produced may flow to a point which acts as a cathode where oxygen is reduced to OH⁻ as follows:

$$\tfrac{1}{2}O_2 + H_2O + 2e^- \rightarrow 2OH.$$

Adding the two half-reactions:

$$\frac{\begin{array}{l}Fe \rightarrow Fe^{2+} + 2e^- \\ 1/2 O_2 + H_2O + 2e^- \rightarrow 2OH^-\end{array}}{Fe + 1/2 O_2 + H_2O \rightarrow Fe^{2+} + 2OH^-}(\rightarrow Fe(OH)_2).$$

The ferrous hydroxide, $Fe(OH)_2$, may then be oxidized to ferric hydroxide, $FeO(OH)$, which may lose water to form ferric oxide, $Fe_2O_3$.

One method of inhibiting the corrosion of steel is galvanization, wherein the steel is coated with elemental zinc, a more active metal. Zinc, being a better reducing agent than iron, protects the iron by reversing the reaction for the formation of $Fe^{2+}$:

$$\frac{\begin{array}{ll}Fe^{2+} + 2e^- \rightarrow Fe & \mathcal{E}^0 = 0.763V \\ Zn \rightarrow Zn^{2+} + 2e^- & \mathcal{E}^0 = -0.440V\end{array}}{Zn + Fe^{2+} \rightarrow Zn^{2+} + Fe \quad \mathcal{E}^0 = 0.323V.}$$

Hence, the zinc coating corrodes sacrificially but the structural iron in contact with the zinc is unaffected as long as the zinc lasts. Small gaps in the zinc exposing the underlying iron are protected by the galvanic action of the zinc. Where the corrosion of zinc leaves large gaps (or where defects otherwise exist in the galvanic coating) the corrosion of iron can occur normally.

One prior art method of evaluating corrosion resistance is to perform accelerated corrosion testing such as a salt fog or salt spray test wherein the component is placed in a corrosive environment having predefined conditions and using predetermined procedures. One drawback of such tests is that they are generally time consuming, often requiring weeks or months to complete. Another drawback to the prior art salt fog tests is that they do not take into account fatigue or cyclic deformation of the metals. It has been found in accordance with the present invention that corrosion is accelerated at points undergoing mechanical fatigue.

One method of predicting cable life under fatigue conditions might be to subject cable to repeated fatigue stresses or strains until the cable fails due to fatigue/corrosion interaction, i.e., until the cable breaks. Such testing may be performed under conditions at which corrosion is accelerated, such as conditions similar to salt fog conditions. However, testing until failure would be a very time consuming process. Therefore, it would be highly desirable to provide an apparatus and method for testing cable that may be used to accurately predict cable life, but that can be performed in a period of time significantly shorter than the time required to test until cable failure.

SUMMARY OF THE INVENTION

The numerous objects and advantages of the present invention are provided by a method and apparatus according to the present invention for the detection and quantifying of localized corrosion of galvanized steel cable. The resistance of galvanized steel cable to corrosion is critical to the manufacture of automotive components for access control, doors, and windows, and the like, as well as other applications, such as aerospace and marine applications, where cables are employed in corrosive environments. Other uses for galvanized cable include, but are not limited to, components for bicycles, flight control avionics, scaffolding, rigging, climbing devices, descent control and fall arrester devices, rescue devices, sailing/marine rigging, gym equipment, bridges, and so forth.

It has been found, in accordance with the present invention, that mechanical/tribological processes couple to corrosion so as to diminish cable life during fatigue in corrosive environments. The corrosion products further accelerate corrosion by decreasing strand-to-strand lubrication and often act as abrasives. Non-homogeneous electrochemical kinetics occur at the surface of a cable that undergoes fatigue in the presence of a corrosive environment. Fatigue and wear activate galvanic corrosion. The resulting currents lead to inhomogeneous fields at the surface of the cable. A variety of electrochemical probes may be employed to detect the electrochemical inhomogeneities produced by the coupling of the corrosion kinetics to the fatigue and wear processes. These probes include scanning ac electrochemical probes (H. Isaacs and M. Kendig, *Corrosion*, 36, 269 (1980)); scanning vibrating electrochemical probes (Isaacs et al., *Corrosion '95*, Paper No. 393 (1995)); scanning dc electrochemical probes (W. Jaenicke and K. Bonhoffer, *Z. Physik. Chem.*, 191,350 (1943)); or scanning Kelvin probes (W. Furbeth and M. Strattmann, Fresenius' J. of Anal. Chem., 353,337 (1995)). Each of the aforementioned references are hereby incorporated by reference in their entireties. The Kelvin probes can be used for relatively "dry" conditions whereas the others are more applicable to electrolytic conditions.

In order to quantify the localized corrosion processes that couple directly to cable fatigue, we have made use of a form of scanning electrochemical probe similar to that described by Isaacs et al. for characterizing localized corrosion including weld HAZ, organic coatings, pitting in stainless steels, corrosion fatigue cracking and initiation of corrosion in galvanized coatings. The basis for this approach appears in FIG. 1 that shows a schematic for a defect in a galvanic coating. The defect is a site for the selective cathodic reduction of oxygen:

$$\tfrac{1}{2}O_2 + H_2O + 2e^- \rightarrow 2OH^-$$

that drives the corrosion of the zinc coating,

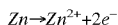

Since the cathode is highly localized, in an electrolyte of finite resistivity, the fields are not homogeneous and their gradients are proportional to localized current density. Hence the voltage signal of the probe relative to the cable scanned at a position z from the surface of a material undergoing localized corrosion will be proportional to the intensity of localized corrosion. In a preferred embodiment, the present invention may be implemented for a cable undergoing mechanical fatigue using a novel weir cell, and the resulting time-dependent signal senses the onset of localized corrosion synchronous with the fatigue cycle. Frequency transformation of the signal is most useful in quantifying the components of localized corrosion, and the evolution of the individual sinusoidal frequency components is useful in predicting the corrosion acceleration factor of the fatigue.

The apparatus of the present invention may be modified to permit rapid electrochemical inspection of entire nins of cable. The weir cell according to the present invention may be used with a probe to detect the dc current associated with the localized corrosion, the impedance/admittance of the cable, or both.

In yet another aspect of the present invention, corrosion cable life may be extended by the selective protection of the high fatigue regions. Protection may be accomplished by identifying the area or areas of cable that will be subjected to fatigue in a given application, typically those areas bent around pulleys or guides, and supplying a protectant such as a grease, lubricant, corrosion inhibitor, passivating agent, or combinations thereof. Methods of application include application of an additional protectant directly to the fatigue regions, e.g., manual application in the form of a gel, the use timed-release formulations that may be, for example, incorporated into the fatigue- or wear-causing component such as a pulley or the like, or through continuous application of a corrosion protectant, for example, from a reservoir from which a protectant may be continuously supplied to the fatigue regions. Also, the pulley itself may be a galvanically comprise a galvanically active metal or may contain a means for applying an impressed current to the high fatigue region of the cable so as to galvanically protect the cable.

It is to be understood that both the foregoing general description and the following detailed description are exemplary and explanatory only and are not restrictive of the invention as claimed. The accompanying drawings, that are incorporated in and constitute a part of the specification, illustrate particular embodiments of the invention and together with the general description, serve to explain the principles of the invention.

BRIEF DESCRIPTION OF THE DRAWINGS

The detailed description of the invention may be best understood when read in reference to the accompanying drawings wherein.

DETAILED DESCRIPTION OF THE INVENTION

Figure 1:
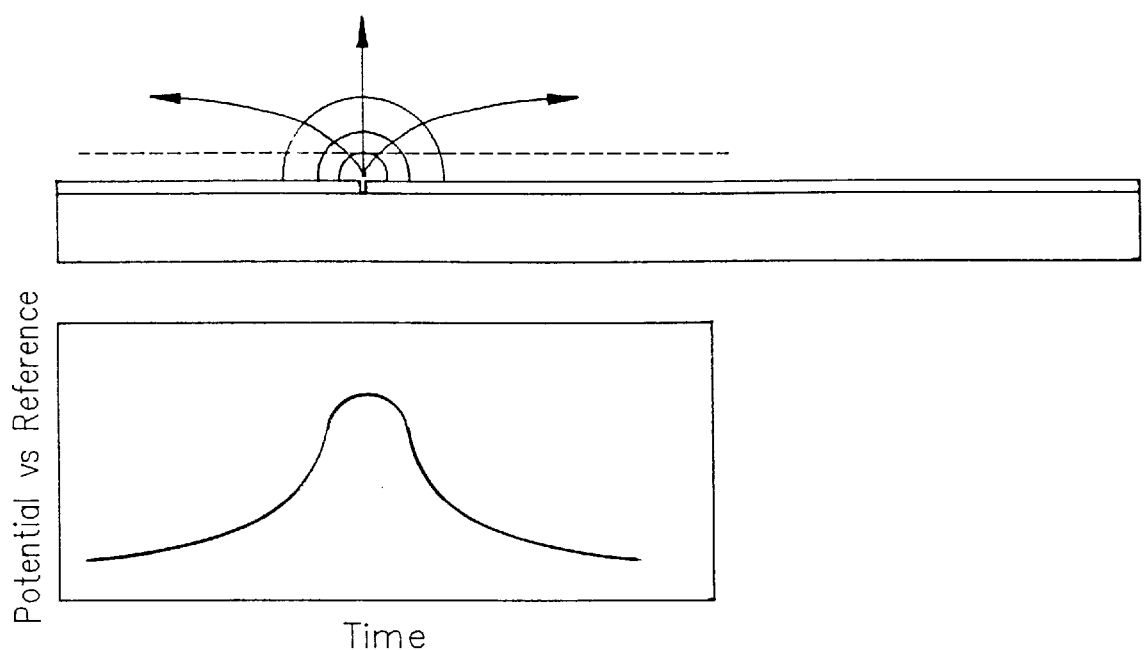
FIG. 1 shows a schematic for defect in a galvanic coating.
Figure 2:
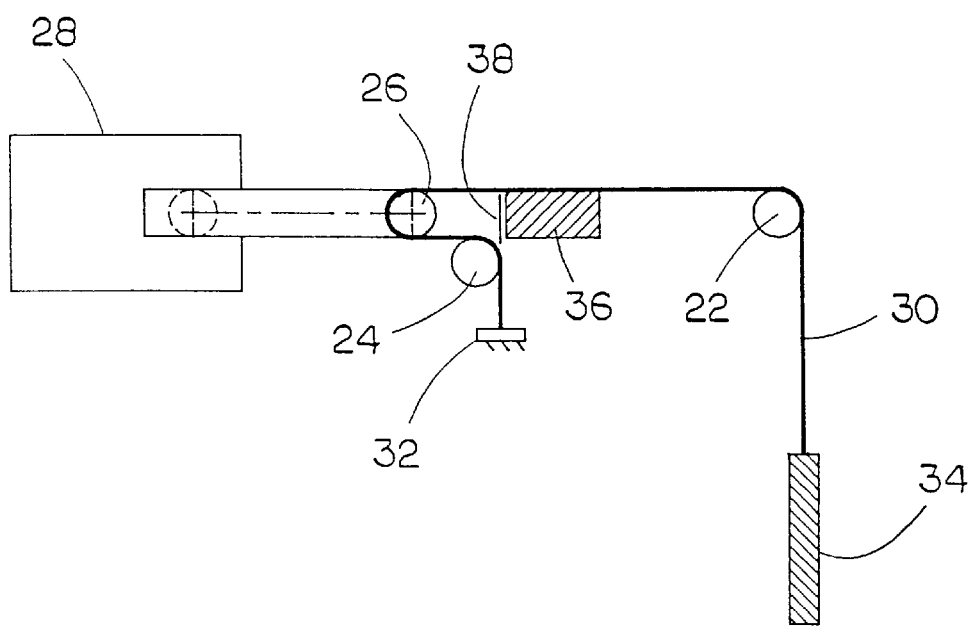
FIG. 2 is a schematic illustration of the fatigue testing apparatus according to the present invention.

Referring now to FIG. 2, the fatigue testing apparatus in accordance with the present invention includes fixed pulleys 22 and 24 and non-fixed pulley 26 controlled by a motion control device 28 such as linear drive stage or other motorized drive as would be known to those skilled in the art. The motion control device 28 may also be interfaced to a computer information handling system such as a general purpose computer, work station, or the like, for motion control and/or recording or logging the number of cycles. Cable 30 is attached at one end to cable anchor 32 and at the other end to load 34. Cable 30 passes around pulleys 22, 24, and 26, and through weir cell 36 containing an electrolyte solution and reference or pseudo-reference electrode 38. The motion control device 28 causes cable 30 to move along the pulleys under tension provided by load 34 in a back and forth manner. In one embodiment, weir cell 36 is continuously refreshed with a 5% aqueous NaCl solution (the concentration of NaCl specified in American Society for Testing and Materials (ASTM) B117 salt fog standards), although it will be recognized that other electrolytes and/or concentrations may be used. For example, the solution may be selected to simulate particular environmental conditions, such as environmental conditions to which the cable to be tested may be exposed in a given cable application. In a preferred embodiment, the pulley configuration and the length of travel of the drive stage or other motion control device 28 are such that portions of the cable 30 experiencing fatigue as well as portions of the cable not experiencing fatigue, i.e., not passing around any pulley, will pass through weir cell 36 for monitoring of the electrochemical response by reference electrode 38. The changing of the pulley diameters provides changes in strain and, thus, cable life (i.e., the smaller the diameter of the pulley, the greater the strain and the shorter the life of the cable).

Figure 3A:
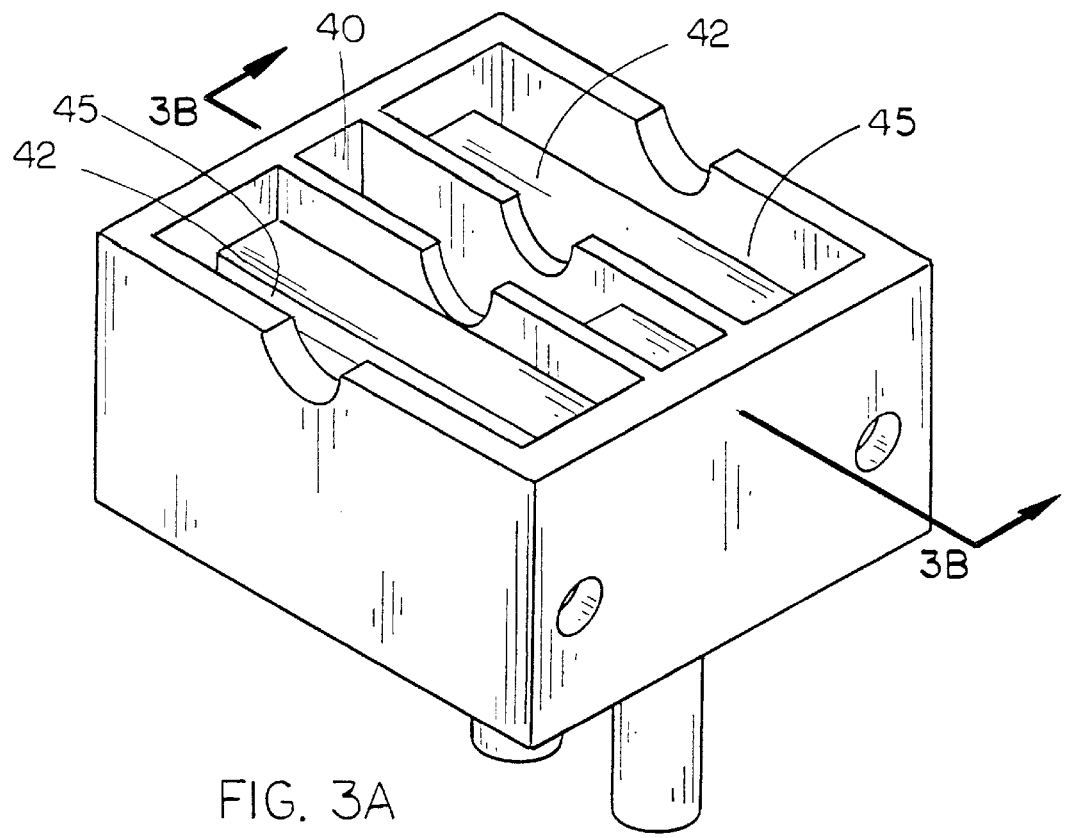
FIGS. 3A and 3B show a preferred weir cell according to the present invention.
Figure 3B:
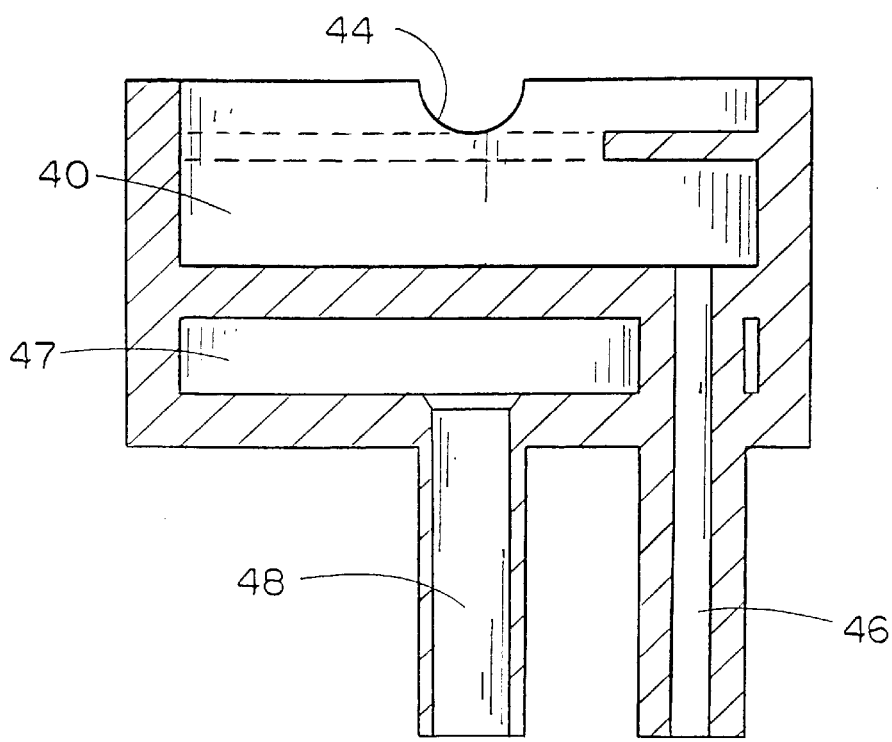

A preferred weir cell apparatus according to the present invention is shown in greater detail in FIGS. 3A and 3B. The cell preferably wets an approximately 3.75 cm length of cable 30 (FIG. 2) as it passes through the weir. The dimension of the portion of electrolyte inlet chamber 40 through which the cable passes may be smaller than the length of cable desired to be wetted. For example, when the wetting region of inlet chamber 40 was about 0.5 cm, it was found that surface tension kept a layer of electrolyte on the shelf regions 42 as it overflowed from slot regions 44 through which the cable passes, over shelf regions 42, and through return openings 45, so that the 3.75 cm length of cable was continuously wetted. Wicking moved the electrolyte into an even much larger length of the cable throughout the individual strands of the cable. Electrolyte solution is continually refreshed by pumping through inlet 46. Overflow electrolyte is drained through return openings 45 into lower return chamber 47 and is removed from the weir through outlet 48.

The weir cell contains a reference electrode 38 (FIG. 2) held in the electrolyte next to the moving cable. Any reference or pseudo-reference electrode may be employed. The reference or pseudo-reference electrode should be positioned close to, but not touching the cable. Preferably, the electrode is placed as close as possible to the electrode without touching the cable. Typically, the distance will be about 1 mm or less. In the event that a current is to be monitored, the weir cell may further contain a counter electrode (not shown). The counter electrode may be, for example, a noble metal electrode.

Figure 6:
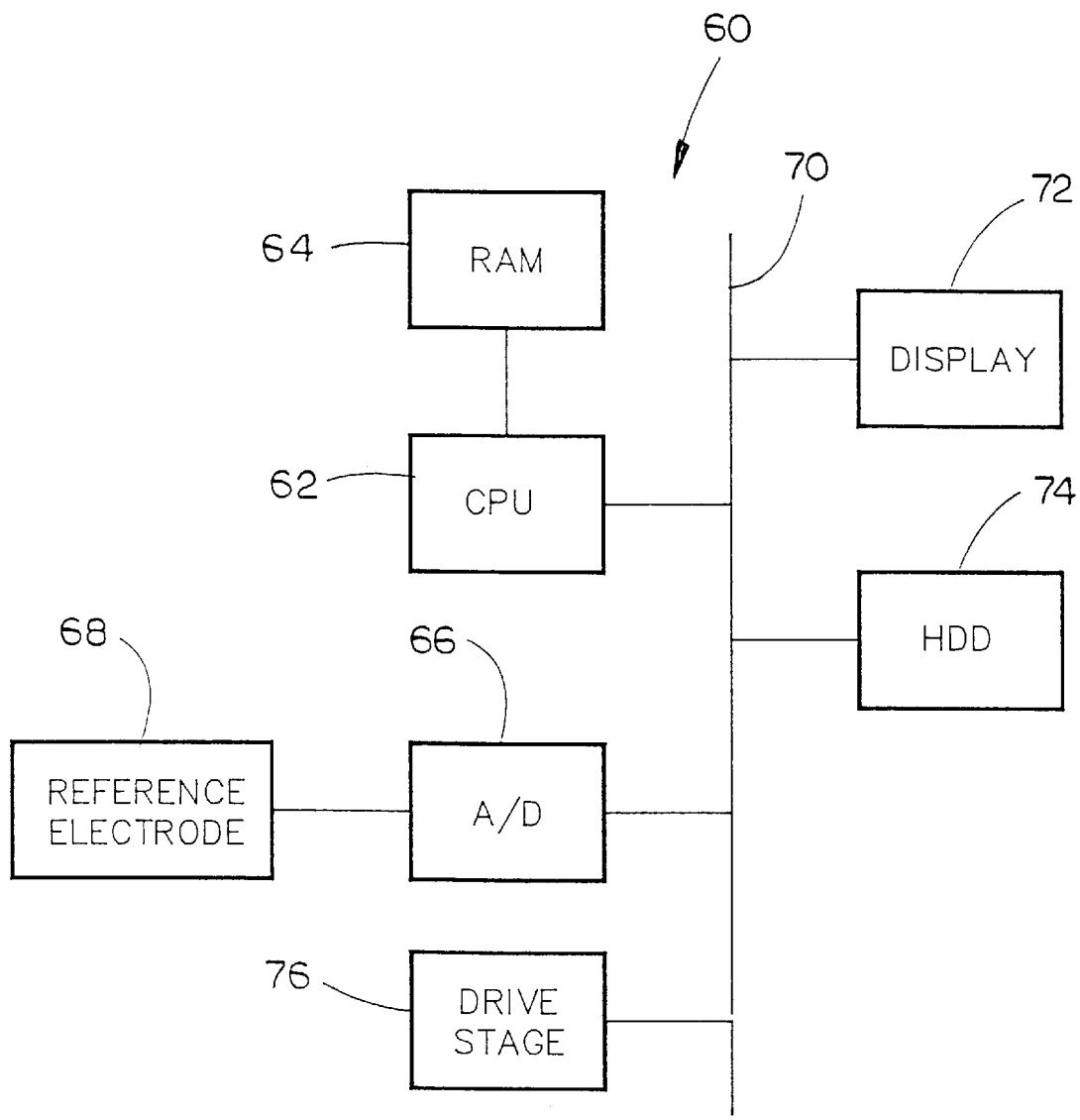
FIG. 6 is a schematic illustration of the apparatus according to the present invention.

Referring now to FIG. 6, a hardware system operable to embody the present invention is shown. The hardware system 60 shown in FIG. 6 is generally representative of the hardware architecture of a computer-based information handling system of the present invention. The hardware system 60 is controlled by a central processing system 62. The central processing system 62 includes a central processing unit such as a microprocessor or microcontroller for executing programs, performing data manipulations and controlling the tasks of the hardware system 60. Communication with the central processor 62 is implemented through a system bus 70 for transferring information among the components of the hardware system 60. The bus 70 may include a data channel for facilitating information transfer between storage and other peripheral components of the hardware system. The bus 70 further provides the set of signals required for communication with the central processing system 62 including a data bus, address bus, and control bus. The bus 70 may comprise any state of the art bus architecture according to promulgated standards, for example industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and so on. Other components of the hardware system 70 include main memory 64, and auxiliary memory 74. The hardware system 60 may further include an auxiliary processing system (not shown) as required. The main memory 64 provides storage of instructions and data for programs executing on the central processing system 62. The main memory 74 is typically semiconductor-based memory such as dynamic random access memory (DRAM) and/or static random access memory (SRAM). Other semi-conductor-based memory types include, for example, synchronous dynamic random access memory (SDRAM), and so on. The auxiliary memory 74 provides storage of instructions and data that are loaded into the main memory 64 before execution. The auxiliary memory 74 may include semiconductor based memory such as read-only memory (ROM), programmable read-only memory (PROM), erasable programmable read-only memory (EPROM), electrically erasable read-only memory (EEPROM), or flash memory (block oriented memory similar to EEPROM). The auxiliary memory 74 may also include a variety of nonsemiconductor-based memories, including but not limited to magnetic tape, drum, floppy disk, hard disk, optical laser disc, compact disc read-only memory (CD-ROM), write once compact disc (CD-R), rewritable compact disc (CD-RW), digital versatile disc read-only memory (DVD-ROM), write once DVD (DVD-R), rewritable digital versatile disc (DVD-RAM), etc. Other varieties of memory devices are contemplated as well. The hardware system 60 may optionally include an auxiliary processing system (not shown) which may be a digital signal processor (a special-purpose microprocessor having an architecture suitable for fast execution of signal processing algorithms), a back-end processor (a slave processor subordinate to the main processing system), an additional microprocessor or controller for dual or multiple processor systems, or a coprocessor.

The hardware system 60 further includes a display system 72. The display system 72 may comprise a video display adapter having all of the components for driving the display device, including video memory, buffer, and graphics engine as desired. Video memory may be, for example, video random access memory (VRAM), synchronous graphics random access memory (SGRAM), windows random access memory (WRAM), and the like. The display system may comprise a cathode ray-tube (CRT) type display such as a monitor or television, or may comprise an alternative type of display technology such as a liquid-crystal display (LCD), light-emitting diode (LED) display, gas or plasma display, electroluminescent display, vacuum fluorescent display, or cathodoluminescent (field emission) display.

An input/output system provides interface functions between the one or more I/O devices, for example, A/D converter 66 and reference electrode 68. The I/O system may also provide interface functions for the motion control device 76., e.g., for controlling the motion control device, for the logging the number of cycles, and/or for correlating the captured signal with the number of cycles. The input/output system may comprise a serial port, parallel port, universal serial bus (USB) port, IEEE 1394 serial bus port, infrared port, network adapter, printer adapter, radio-frequency (RF) communications adapter, universal asynchronous receiver-transmitter (UART) port, etc., for interfacing between corresponding I/O devices such as a keyboard, mouse, trackball, touchpad, joystick, trackstick, infrared transducers, printer, modem, RF modem, bar code reader, charge-coupled device (CCD) reader, scanner, compact disc (CD), compact disc read-only memory (CD-ROM), digital versatile disc (DVD), video capture device, touch screen, stylus, electroacoustic transducer, microphone, speaker, etc. The input/output system and I/O devices may provide or receive analog or digital signals for communication between the hardware system 60 of the present invention and external devices, networks, or information sources. The input/output system and I/O devices preferably implement industry promulgated architecture standards, including Ethernet IEEE 802 standards (e.g., IEEE 802.3 for broadband and baseband networks, IEEE 802.3 z for Gigabit Ethernet, IEEE 802.4 for token passing bus networks, IEEE 802.5 for token ring networks, IEEE 802.6 for metropolitan area networks, and so on), Fibre Channel, digital subscriber line (DSL), asymmetric digital subscriber line (ASDL), frame relay, asynchronous transfer mode (ATM); integrated digital services network (ISDN), personal communications services (PCS), transmission control protocol/Internet protocol (TCP/IP), serial line Internet protocol/point to point protocol (SLIP/PPP), and so on. It should be appreciated that modification or reconfiguration of the hardware system 60 of FIG. 6 by one having ordinary skill in the art would not depart from the scope or the spirit of the present invention.

In one embodiment, a zinc wire pseudo-reference electrode in a Luggin capillary was used as the reference electrode. The tip of the Luggin capillary was set to within less than 1 mm of the cable. The test electrolyte filled the Luggin. In an alternative embodiment, a zinc wire placed less than 1 mm from the cable in the wetted zone of the lip of the weir was used as the reference electrode.

The potential between the reference electrode and the cable was continuously monitored using a high-speed analog-to-digital converter. Samples of typically 25 cycles were recorded and processed as follows: subtraction of the average, application of a Hanning filter, and extraction of harmonic magnitudes. The zinc wire is preferred as a reference because it was found to minimize the bias between it and the cable but held nearly a constant dc potential over many fatigue cycles (100 or more). Typically every 10 samples of 20–25 cycles were saved for post processing. It will be recognized that an amplifier may be employed to amplify the voltage signal from the reference electrode to a suitable level for the A/D converter being used. Other analog signal processing circuitry may also be employed, such as an anti-aliasing filter to remove undesired higher frequency signals which may interfere with subsequent digital processing of the signal. In one embodiment, the reference electrode was connected to an isolation amplifier with a gain setting of 10× and a 4 Hz low pass filter. In order to eliminate cross-talk from the motor, the reference electrode and cable leads were connected directly to the A/D device by a shielded twisted pair of conductors. The A/D converter was interfaced directly to a general purpose CPU for signal processing.

In one embodiment, a central processing unit may be utilized to perform the digital signal processing functions. Any general purpose computer processor may be used for digital signal processing. Although not as efficient as digital signal processors, a general computer processor may be used for digital signal processing, in which case all that is required is an analog-to-digital signal converter for providing an interface between the reference electrode and the central processing unit.

In other embodiments of the present invention, the output of the analog-to-digital converter may be fed into a digital signal processor (not shown) which performs computationally intensive processing of the digital signal. The output of the digital signal processor (DSP) may then feeds into a general purpose central processing unit where the signal may be further processed and stored in non-volatile memory. The voltage signal may thereby be captured and converted into a digital file.

In still other embodiments, a digital signal processor may be utilized which incorporates essential DSP support functions on a single integrated circuit. The DSP may be selected to include analog-to-digital and digital-to-analog converters on a single integrated circuit. Further, other subcircuits such as amplifiers and anti-aliasing filters may be included on the single integrated circuit of the digital signal processor.

Any number of fatigue test configurations can be used. For example, the setup shown in the schematic in FIG. 2 shows a tension-tension test. In this configuration, the cable tracks around pulley 22, bending under tension at the outermost fibers. The configuration shown in FIG. 2 is advantageous in that it allows both a portion of the cable that passes around the pulley experiencing high stress/strain and a portion that does not experience the fatigue to pass by the reference probe electrode. Hence, the reference probe senses both the corrosion potential of both portions of the cable and the resulting cyclic signal is recorded.

It will be recognized that the configuration illustrated in FIG. 2 is not limiting of the present invention, but rather is exemplary, illustrative, and explanatory only, and many other test setups will now become apparent to those skilled in the art, including configurations which may be modeled after particular cable applications and environments. For example, a tension-compression type reversed straining and/or combinations thereof and may be employed to simulate actual design applications or material property data.

As an example, fatigue experiments were performed on both a degreased and as received Berger 1.8 mm S cable, and a Young Heung 1.5 mm cable. The degreased Berger cable failed after 16.5 kilocycles of fatigue while the as-received Berger cable required 18.2 kilocycles of fatigue.

Samples to be tested in the degreased condition are degreased by exposure to a condensing vapor of a solvent such as hexane, xylene, and the like. Samples are preferably degreased under a condensing vapor of the solvent, although any method of degreasing may be employed so long as it does not result in the passivation of the zinc coating. Care should be taken when considering alternative decreasing methods since some aqueous degreasing agents may have corrosion inhibitors which would inhibit the zinc corrosion, thereby giving a false reading for the tests of the degreased specimens. Samples to be tested in the as received condition typically have a lubricant applied by the vendor and are and are tested as received from the vendor without degreasing.

Figure 4:
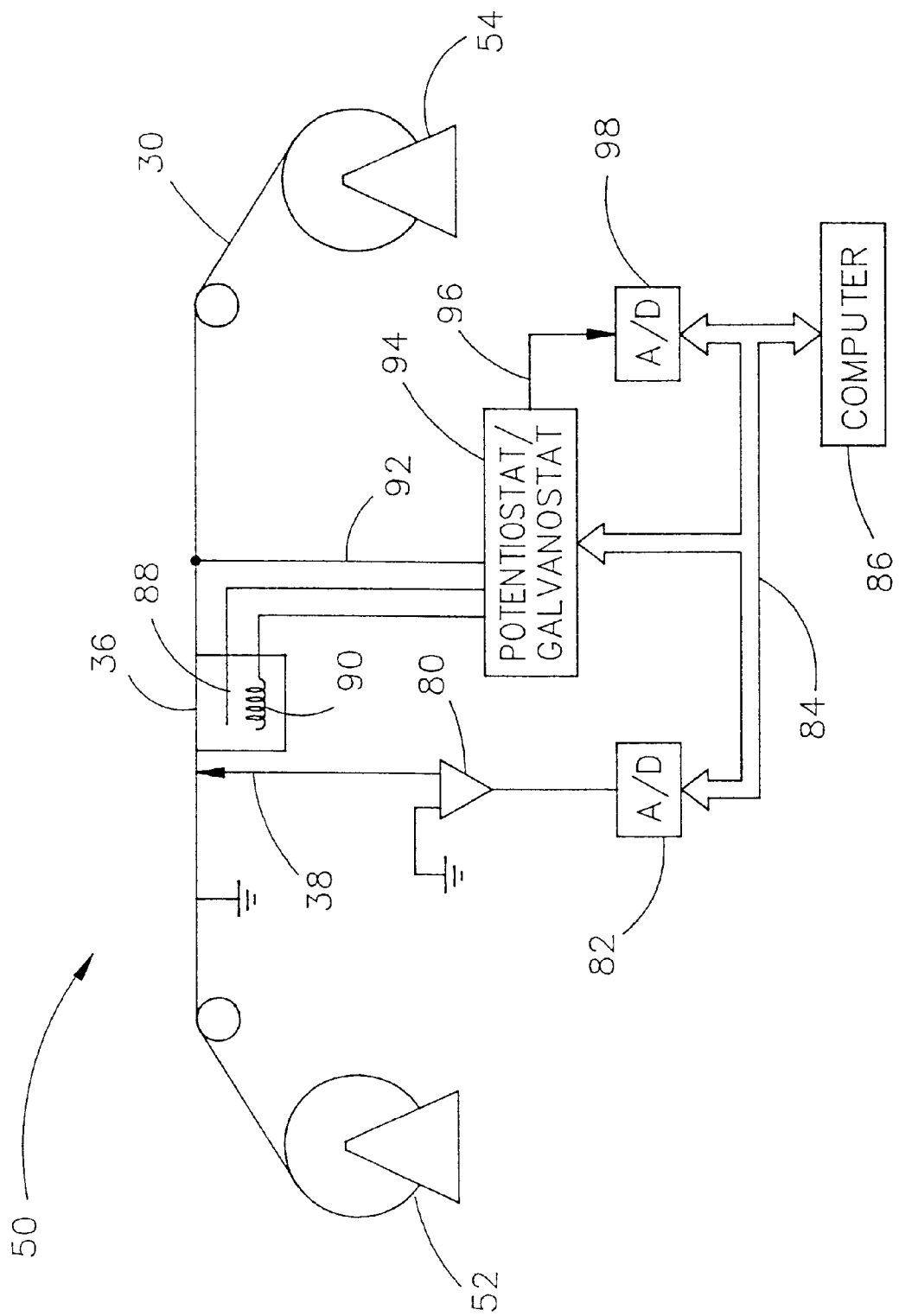
FIGS. 4 and 5 are schematic illustrations of the apparatus according to the present invention for inspecting entire runs of cable.

FIG. 4 shows an exemplary apparatus 50 that may be employed in testing entire runs of cable for localized corrosion. Cable 30 is wound off from supply reel 52 as it passes through weir cell 36 containing electrolyte and is wound onto drivable take-up reel 54. The localized current may be monitored for the entire length of the cable 30 by monitoring the potential appearing between the reference electrode 38 and the cable to be tested. The apparatus of FIG. 4 may optionally further include a degreasing tank 56 (FIG. 5) and a wash tank 58 (FIG. 5) as described below by way of reference to FIG. 5. The electrolyte is preferably corrosively inert. Examples of corrosively inert electrolyte solutions include, but are not limited to solutions containing $NaClO_4$, $NaNO_3$, $Na_2SO_4$, and the like. A preferred corrosively inert electrolyte solution is the buffered sodium molybdate electrolyte disclosed in U.S. application Ser. No. 09/173,088, filed Oct. 14, 1998, incorporated herein by reference in its entirety.

The reference probe 38 signal is amplified by amplifier 80 and the amplified signal is sent to A/D converter 82. The digitized signal is then sent to computer 86 over data bus 84 for further processing and/or storage. The data bus may be for example, IEEE 488 general-purpose interface bus.

In an alternative embodiment of the electrochemical cable inspection apparatus according to the present invention, the weir cell may optionally contain an auxiliary or additional reference electrode 88 and counter electrode 90. Additional or auxiliary reference electrode 88 maybe any suitable reference or pseudo-reference electrode as described above. The auxiliary reference electrode system may be employed in place of, or in addition, to reference probe 38. The counter electrode 90 may be used to measure the interfacial impedance/admittance of the cable (i.e., the admittance/impedance of the cable/electrolyte interface as distinguished from the admittance/impedance of the cable itself) in a buffered molybdate solution or other suitable solution. Briefly, it has been found in accordance with the present invention that the specific electrochemical admittance of iron in the presence of a buffered molybdate solution is much higher than the specific electrochemical admittance of zinc in the same solution. By observing the specific admittance of a cable the quantity of exposed iron active sites can be determined. The use of the impedance/admittance of galvanized steel in a buffered molybdate solution is described in application Ser. No. 09/173,088, incorporated herein by reference. As described in said application Ser. No. 09/173,088, the admittance measurements provide a measure of the exposed iron active sites and thus, zinc porosity. Also, admittance measurements performed on both degreased cable and a cable having a corrosion inhibitor applied allow the calculation of the efficiency of the corrosion inhibitor.

Additional reference electrode 88, counter electrode 90, and cable lead 92 are connected to a potentiostat/galvanostat card 94 interfaced to computer 86 via data bus 84. Current output 96 from potentiostat/galvanostat 94 is representative of the defects in the galvanic zinc coating and may be fed to A/D converter 98 for subsequent processing and/or storage.

In one embodiment, the apparatus shown in FIG. 4 contains both reference electrode 38 and an auxiliary reference electrode 88. In this manner, both the interfacial or electrochemical impedance/admittance of the cable and the dc current of the cable due to localized corrosion may be simultaneously measured as the cable passes throughout the molybdate buffered electrolyte. The impedance of the cable interface is inversely proportional to the porosity of the zinc coating. The use of the impedance/admittance to characterize zinc porosity is described in the above-incorporated application Ser. No. 09/173,088.

Figure 5:
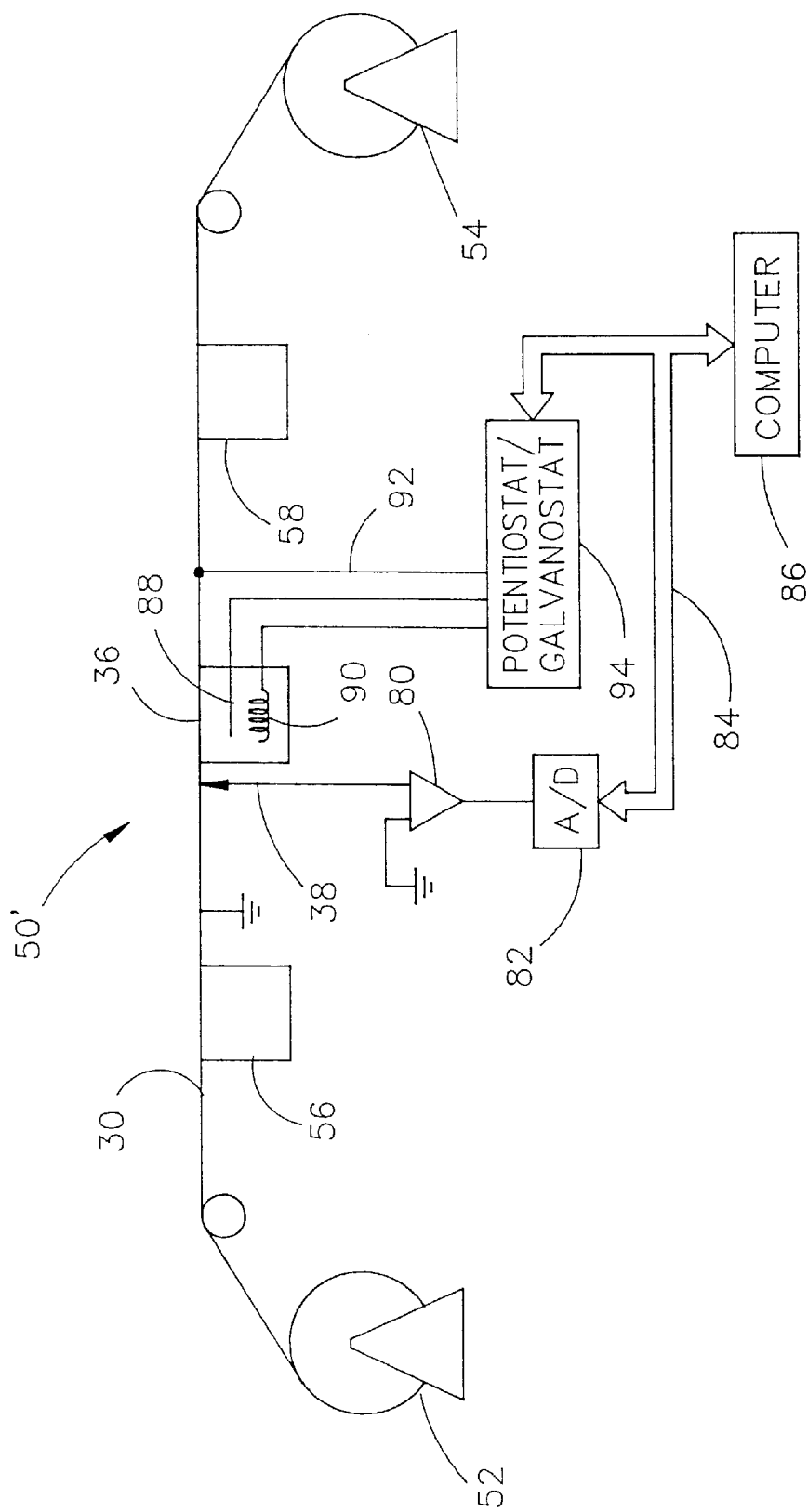

FIG. 5 shows another exemplary apparatus 50' according to the present invention for the electrochemical inspection of entire runs of cable. For example, cable 30 may be degreased prior to electrochemical monitoring in the one or more optional degreasing tanks 56. Also, one or more optional wash tanks 58 may be provided to allow the use of a corrosive electrolyte, such as sodium chloride, in the weir cell 36 during the electrochemical inspection, which may be immediately washed prior to winding cable 30 onto take-up reel 54.

The reference probe 38 signal is amplified by amplifier 80 and the amplified signal is sent to A/D converter 82. The digitized signal is then sent to computer 86 over data bus 84 for further processing and/or storage.

In an another embodiment of the electrochemical cable inspection apparatus according to the present invention, the weir cell may optionally contain an auxiliary reference electrode 88 and counter electrode 90. The auxiliary electrode system may be employed in place of, or in addition, to reference probe 38. Additional reference electrode 88 may be used for measuring the interfacial impedance/admittance of the cable for characterizing zinc porosity of the cable in a buffered molybdate solution, or other suitable electrolyte, as described above and in application Ser. No. 09/173,088, incorporated herein by reference. By measuring admittance of both degreased cable and greased cable , the efficiency of the corrosion inhibitor can be determined.

Additional reference electrode 88, counter electrode 90, and cable lead 92 are connected to a potentiostat/galvanostat card 94 interfaced to computer 86 via data bus 84 for monitoring and storage of the electrochemical admittance along the entire length of cable In one embodiment, the apparatus shown in FIG. 5 contains both a reference electrode 38 and an auxiliary electrode 88. In this manner, both the impedance/admittance of the cable and the dc current of the cable due to localized corrosion maybe simultaneously measured as the cable passes throughout the molybdate buffered electrolyte.

Although the testing apparatus shown in FIGS. 4 and 5 are depicted schematically in a substantially linear configuration, it will be recognized that the apparatus is not limited to any particular physical configuration and that the cable may be tensioned or directed, as with pulleys or other means, as would be understood by those skilled in the art. In a preferred embodiment, the degree of localized corrosion may be recorded as a function of position along the length of the cable. In this manner, areas exhibiting a high degree of localized corrosion, e.g., where there exists a defect in the zinc coating, may be specifically treated with a lubricant, corrosion inhibitor, passivating agent, etc. Also, such sections may be avoided for critical applications or applications undergoing cyclic fatigue in a corrosive environment. The testing apparatus allows for the inspection of 100% of incoming cable may also be used to determine if cable meets certain criteria, for screening vendor supplied cable for quality, and so forth.

In one embodiment according to the present invention, the cable cycler system is controlled via a Macintosh computer and a software developed under the LabVIEW development system. Communication between LabVIEW and the drive stage is implemented via the Macintosh serial port. The computer is equipped with an internal high-performance multifunction I/O board that features a 12-bit A/D converter with eight analog input channels and a maximum sampling rate of 100 kS/s. The multifunction I/O board is in turn interfaced with a SCXI (Signal Conditioning eXtensions for Instrumentation) chassis system that allows for conditioning of any analog signal before digitization. The analog signal from the reference electrode is conditioned via an isolation amplifier configured for 10× amplification with a 3-pole RC low-pass filter configured for 4 Hz.

The software program performs the necessary system hardware initialization and configuration and the most pertinent operations of the software main data acquisition loop are then as follows:
(1) Start a timed A/D data acquisition.
(2) Command the drive stage to perform a cycle.
(3) During the time taken to perform the cycle, process and display data from the previous cycle and perform any necessary I/O functions. Write waveforms to disk for the following cases: (a) cable break; (b) correct cycle multiple; (c) program execution stopped; or (d) first cycle.
(4) Check whether the cable has broke or not.
(5) Wait for drive stage to have completed the cycle.

(6) Acquire corrosion cell data from the A/D board.

(7) Check hardware status and repeat loop if all conditions met.

Figure 7:
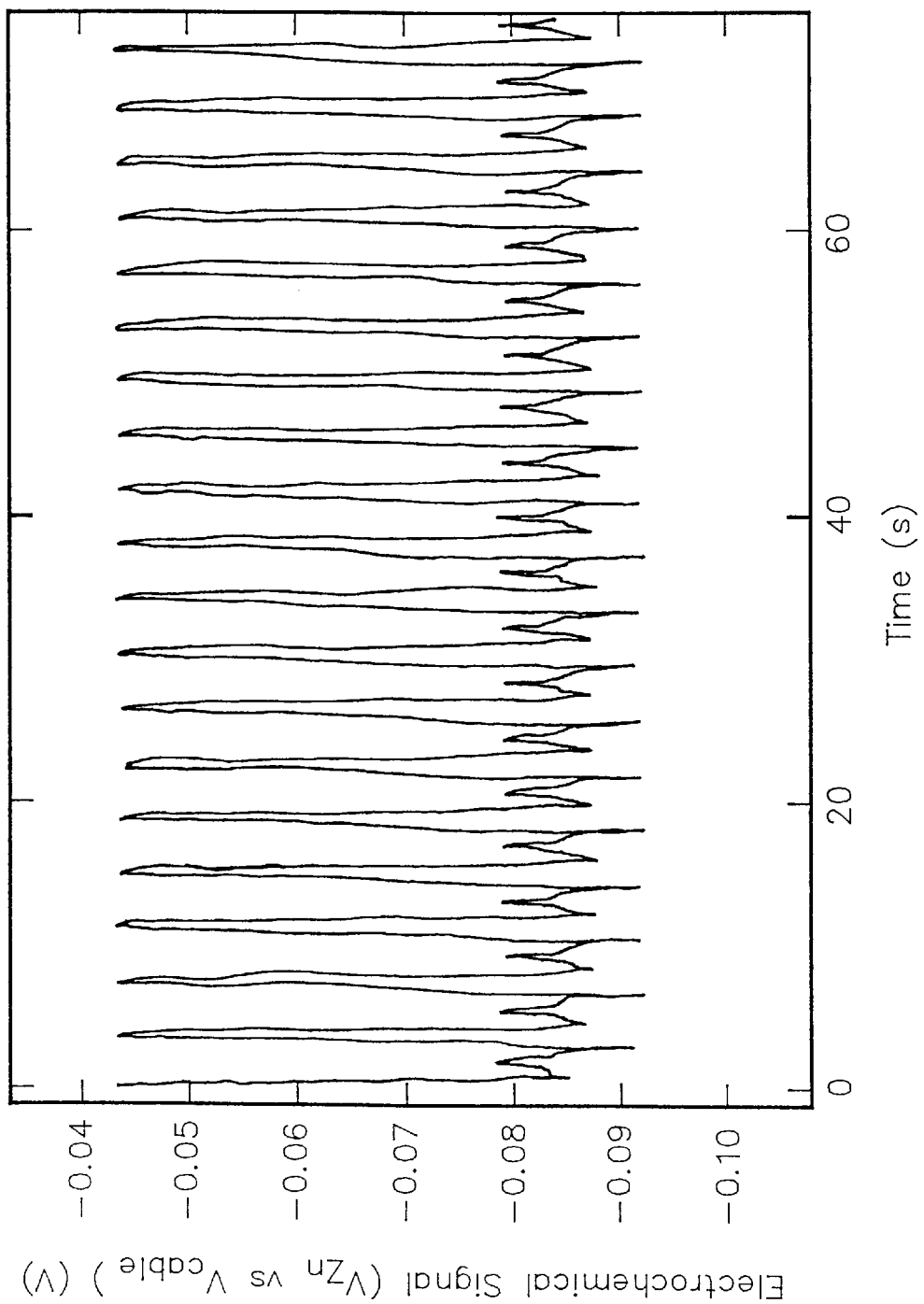
FIG. 7 shows a typical signal for a galvanized-steel cable undergoing fatigue.
Figure 8:
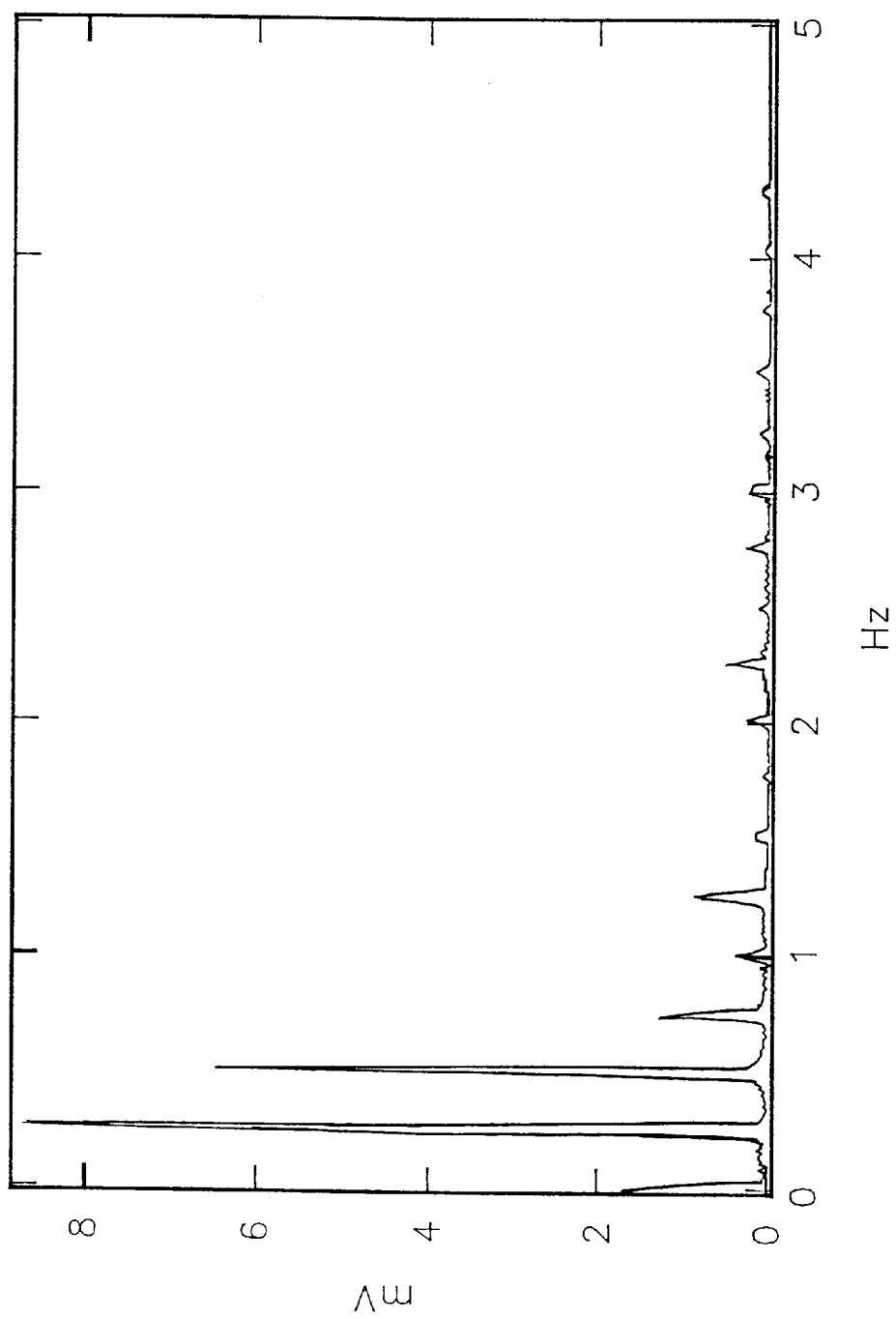
FIG. 8 shows the Fourier transform of the waveform of the cable undergoing fatigue from FIG. 7.

Referring now to the fatigue testing apparatus (FIG. 2), the resulting cyclic electrochemical potential appearing between the reference electrode 38 and the reciprocating cable 30 was collected as a function of cycles. FIG. 7 shows a typical signal for a galvanized-steel cable undergoing fatigue. The respective Fourier transforms of the waveform of the cable undergoing fatigue was made after subtracting an average and applying a Hanning filter to remove the dc. For example, FIG. 8 shows the respective transforms for the waveforms from the data from FIG. 7. The first peak in FIG. 8 is the fundamental that appears at the frequency of the fatigue cycle. The higher order harmonics appear periodically with increasing frequency (FIG. 4). The magnitude of the harmonics provides a useful means for quantifying the pattern as well as intensity of the electrochemical response.

Figure 9:
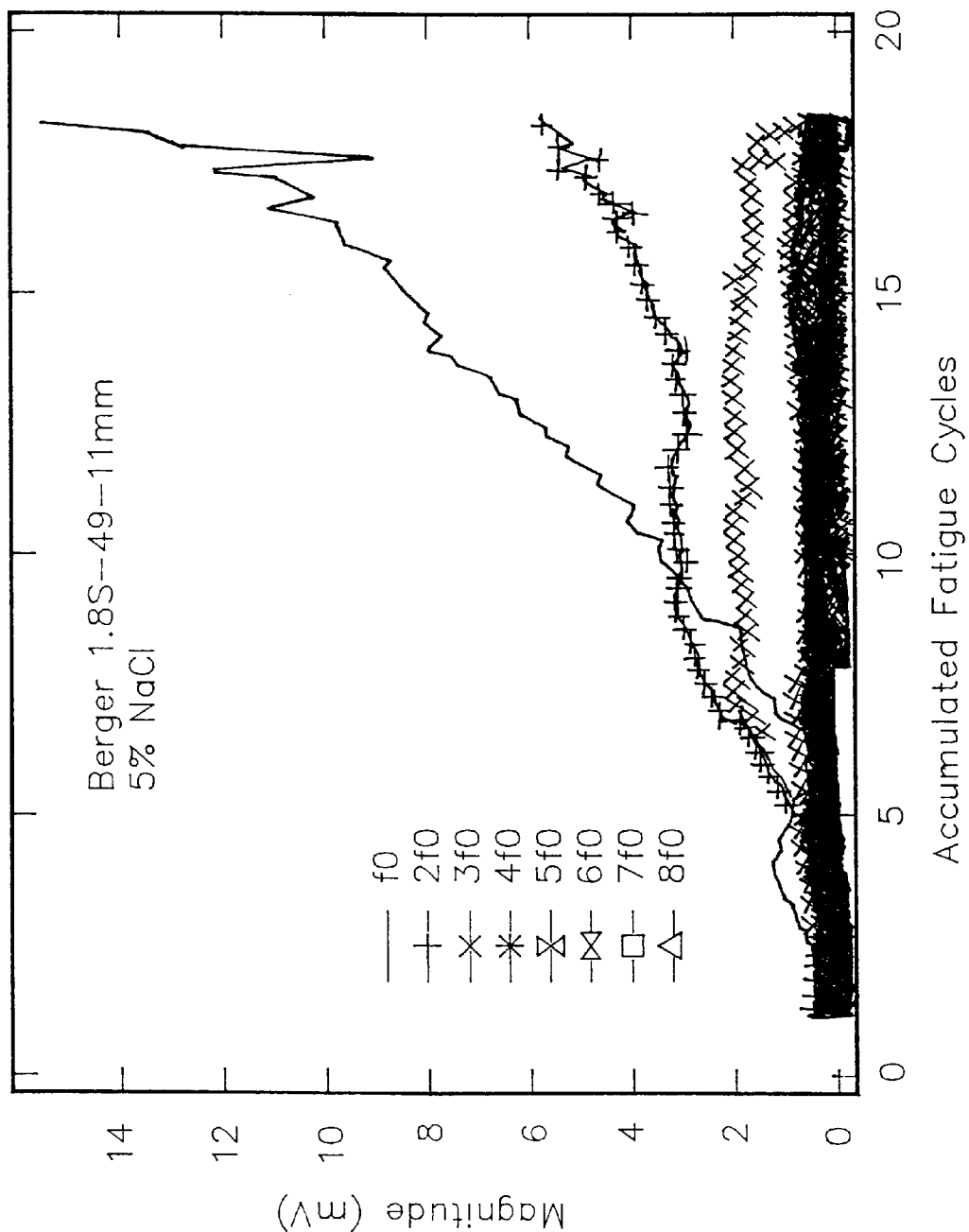
FIG. 9 shows the magnitudes of the first eight harmonics as a function of cycle for the Berger cable.
Figure 10:
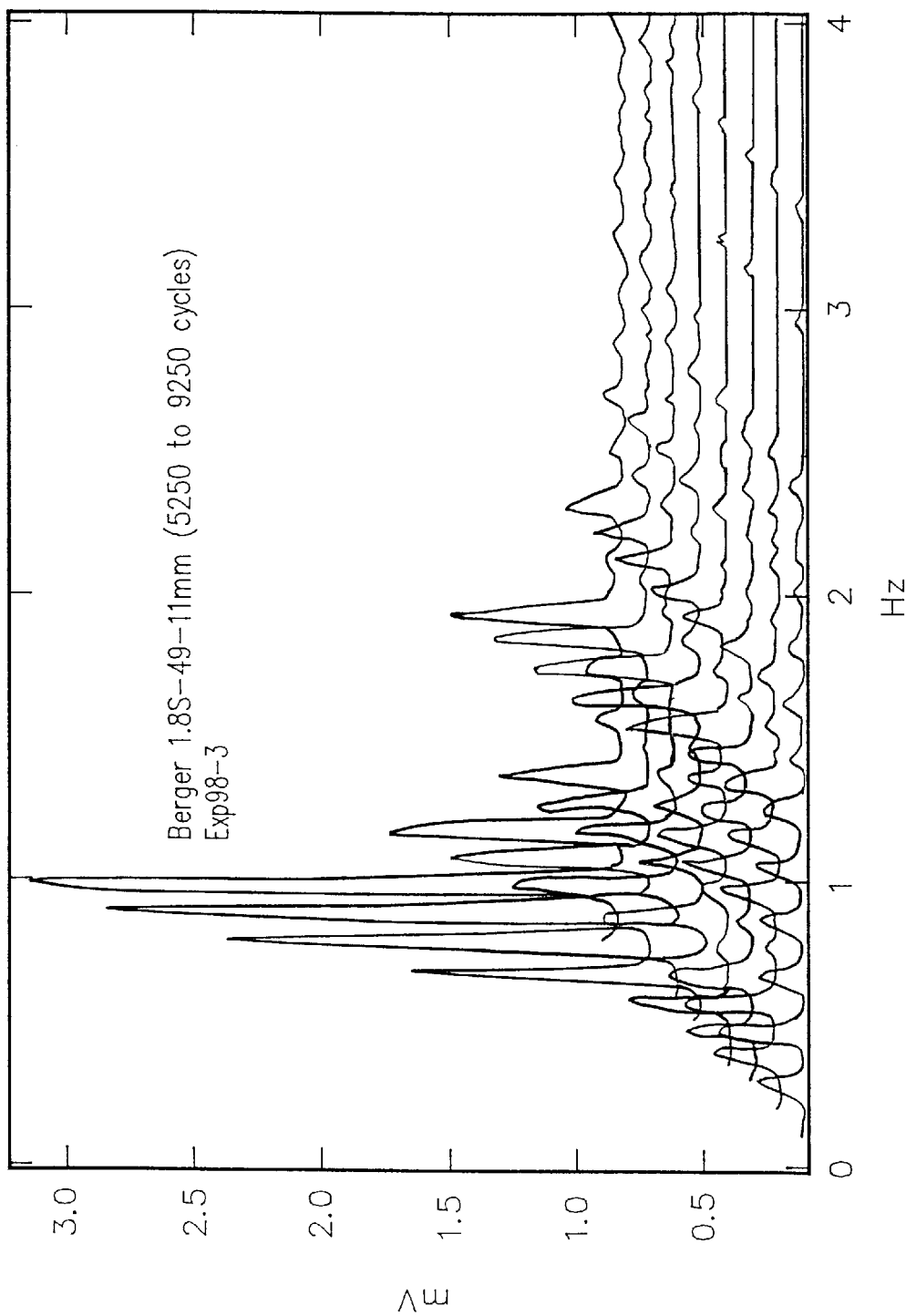
FIG. 10 is a waterfall plot showing the evolution of the frequency spectrum.

The magnitudes of the first eight harmonics appear as a function of cycle for the Berger cable in FIG. 9. At about 5,000 cycles the second and higher harmonics begin to increase while the fundamental shows a more dramatic increase in the vicinity of 7,000 cycles. Both of these characteristics (the fundamental intensity and higher harmonic intensities) initiate well before failure (breakage) of the cable at 18,200 cycles and indicate the initiation of corrosion or breakdown of protection by the lubricant. While not intended to be bound by any particular theory, the appearance of higher harmonics before the fundamental may indicate the nucleation of many sites of fatigue damage which coalesce to one dominant site with time. Nevertheless, the second and third harmonics reach a plateau while the higher harmonics first diminish and then gradually rise toward the end of the test. The second harmonic gradually rises again after 14,000 cycles. A waterfall plot showing the evolution of the frequency spectrum is shown in FIG. 10.

Figure 11:
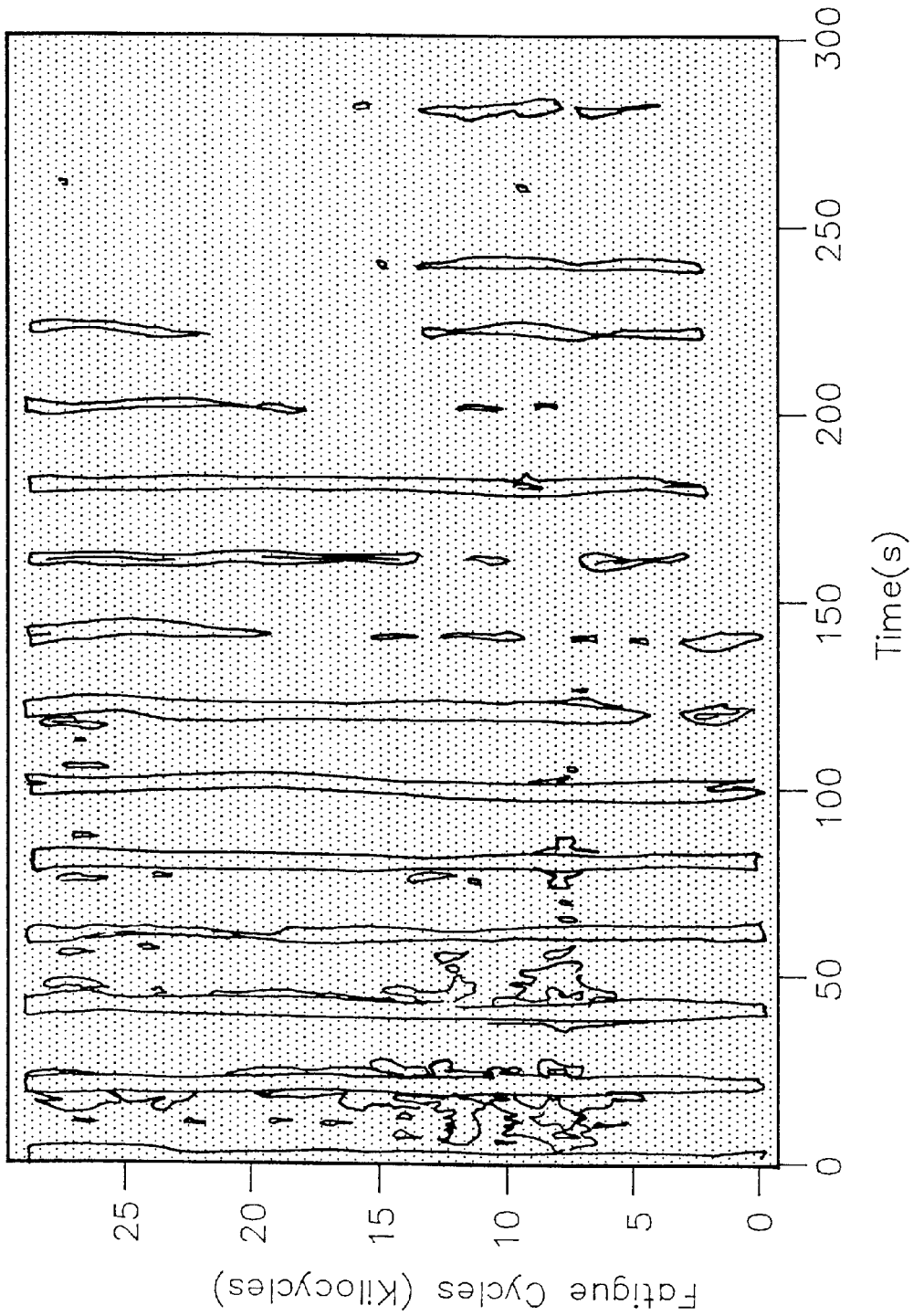
FIG. 11 is three-dimensional contour plot showing the harmonic intensities for the electrochemical signal for a representative material.

Another type of plot that provides details of the features of the cable appears in FIG. 11 for the Young Heung material. This three-dimensional contour plot provides the harmonic intensities for the electrochemical signal with the number of fatigue cycles in the y-direction and the frequency in the x-direction. The Young Heung cable having a relatively thin zinc coating exhibits an early rise in the fundamental and the appearance of significant higher harmonics. This can be seen in FIG. 11.

It has been found in accordance with the present invention that the electrochemical response anticipates the failure of the ability of the zinc coating to galvanically protect against corrosion of the steel filaments. The number of cycles where this occurs can be used to predict the acceleration of cable failure provided by the corrosive environment.

Figure 12:
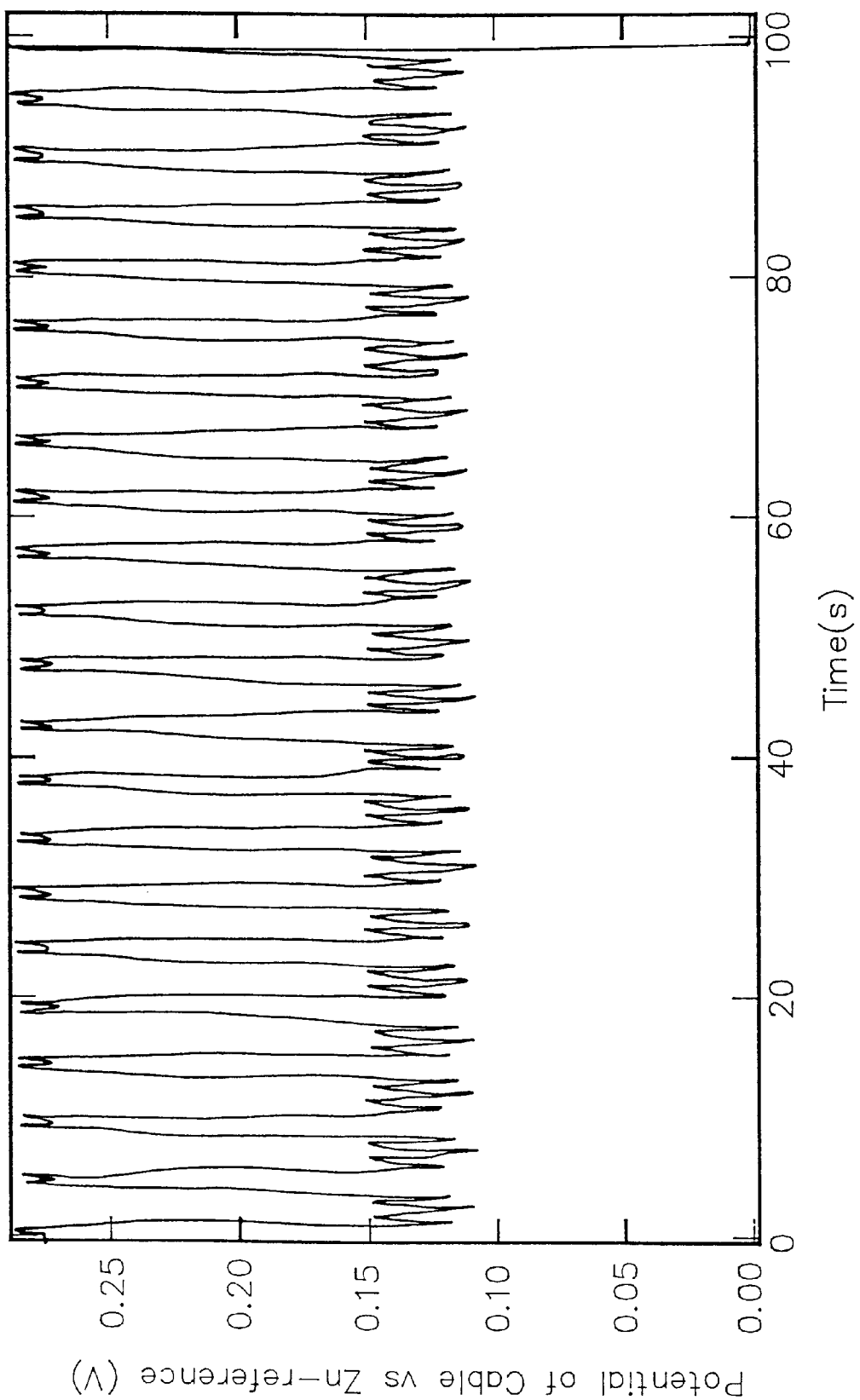
FIG. 12 shows the time dependence for the corrosion potential of the cable referenced to a pure zinc wire electrode as the cable passes near the reference electrode during the fatigue cycle.

FIG. 12 shows the time dependence for the corrosion potential of the cable referenced to a pure zinc wire electrode as the cable passes near the reference electrode during the fatigue cycle. This particular record of data was taken after the metallic zinc had worn from the cable to leave a substantial quantity of iron exposed in the region of highest fatigue. Accordingly, when the fatigue-damaged, iron-rich surface moved next to the reference electrode, a relatively high potential is recorded; whereas, when the reference electrode is beside the part of the cable that is not damaged by fatigue, so as to retain the zinc coating, a lower potential is recorded. Hence, the positive-going oscillations appear in FIG. 12 during the time intervals when the reference is adjacent to the high fatigue region during cycling.

Figure 13:
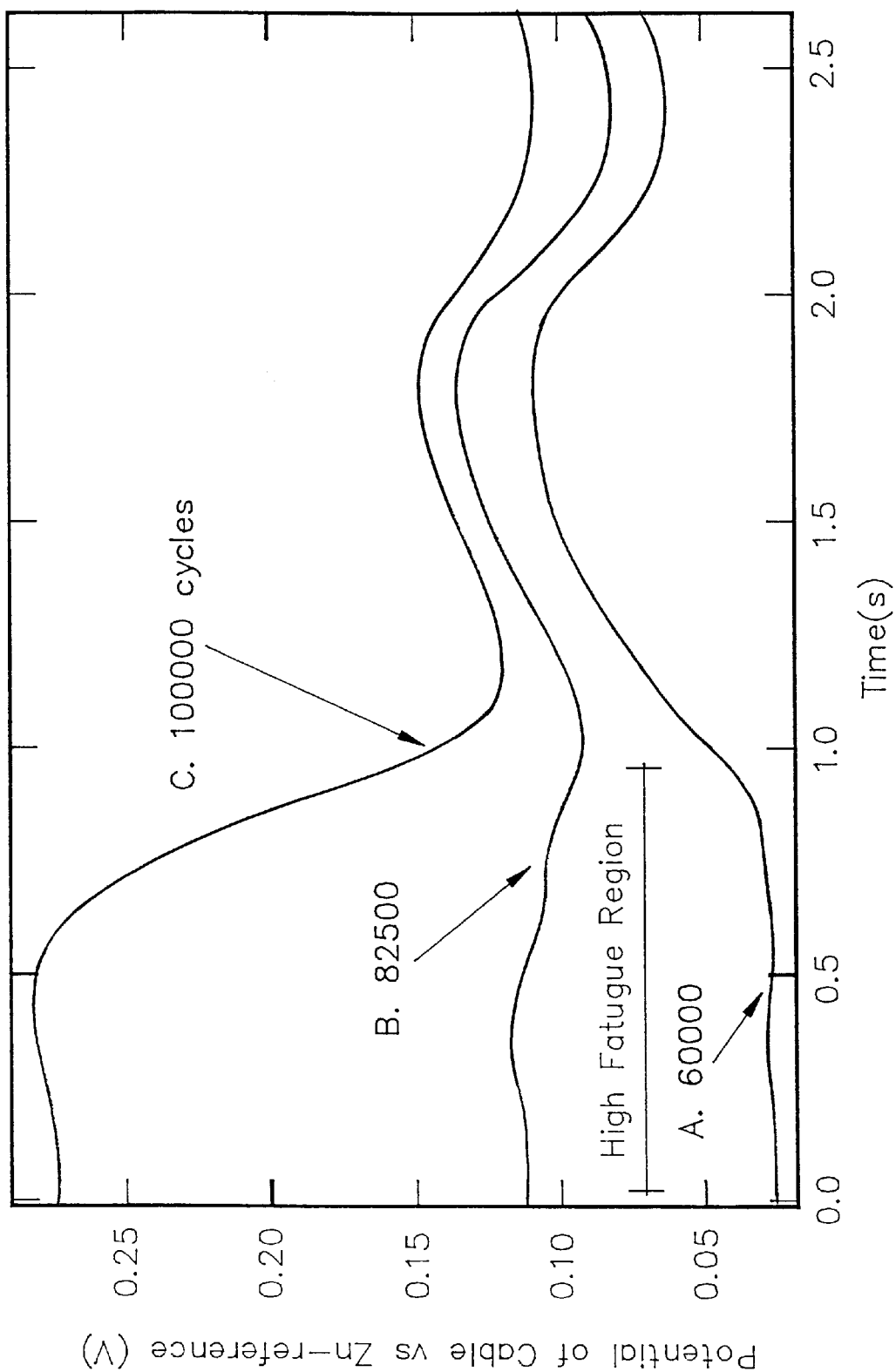
FIG. 13 shows the electrochemical response for single cycles taken at various stages of zinc removal.

This effect is better viewed by looking at the electrochemical response for only one cycle as shown in FIG. 13.

FIG. 13 plots curves taken from cycles before zinc removal (A. 60,000 cycles), after zinc removal (C. 100,000 cycles), and at the critical transition (B. 82,500 cycles). Note that before removal of the zinc (A), the potential of the high fatigue zone falls relative to that in the not-fatigued zone. This results from the fact that the zinc corrosion in the fatigue zone accelerates due to mechanical and tribo-depassivation. After the zinc has worn from the cable in the fatigue region, the fatigue region becomes iron rich. Since the galvanic potential for iron is substantially above that for the zinc, curve C shows a significantly higher potential in the fatigue region shown by curve C in FIG. 7. Between cases (A) and (C) a transition occurs (B). At this transition the amplitude of the electrochemical response changes phase and reaches a minimum.

Figure 14:
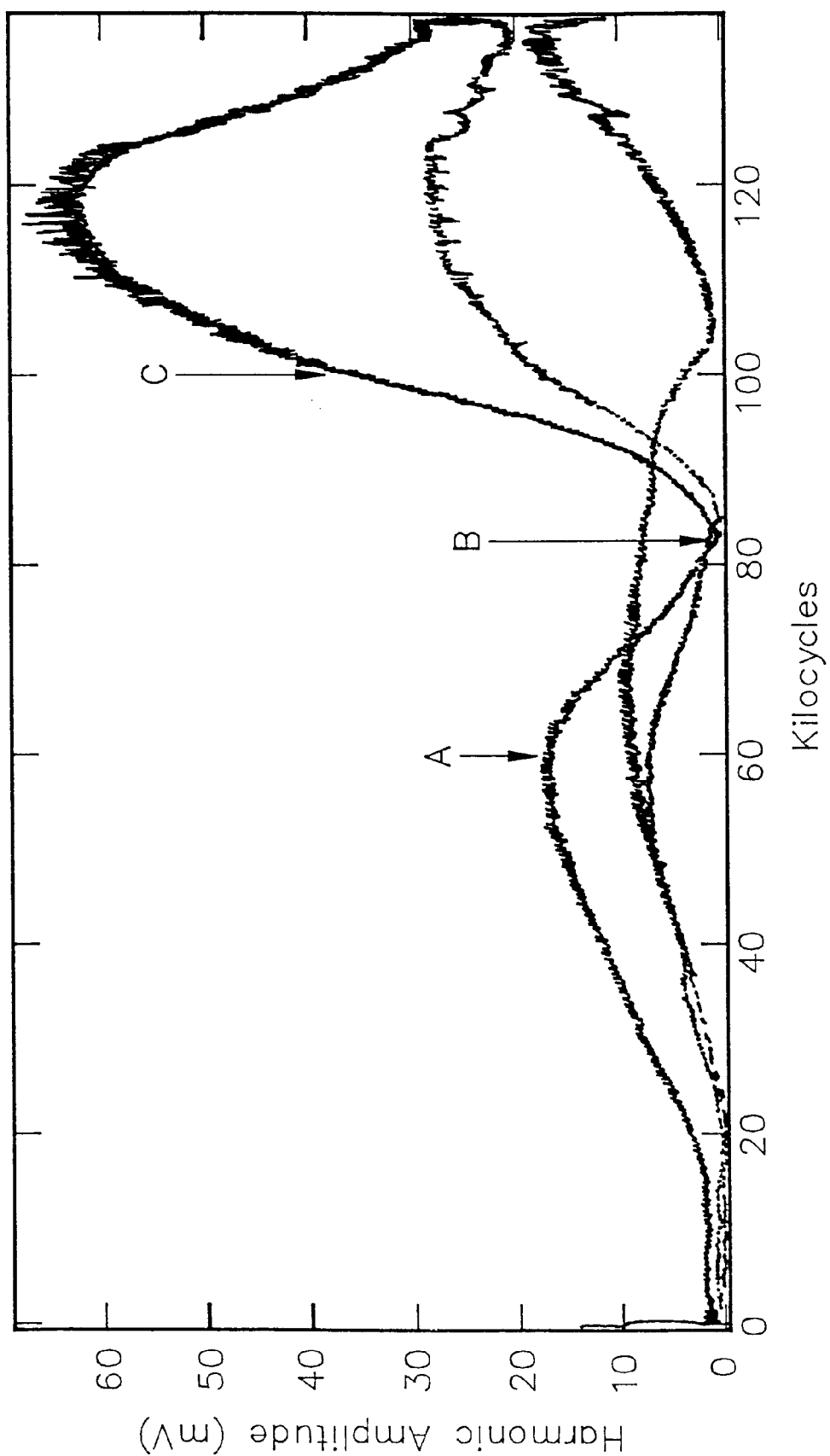
FIG. 14 shows the fundamental and the first two harmonics of the cyclic electrochemical potential response.
Figure 15:
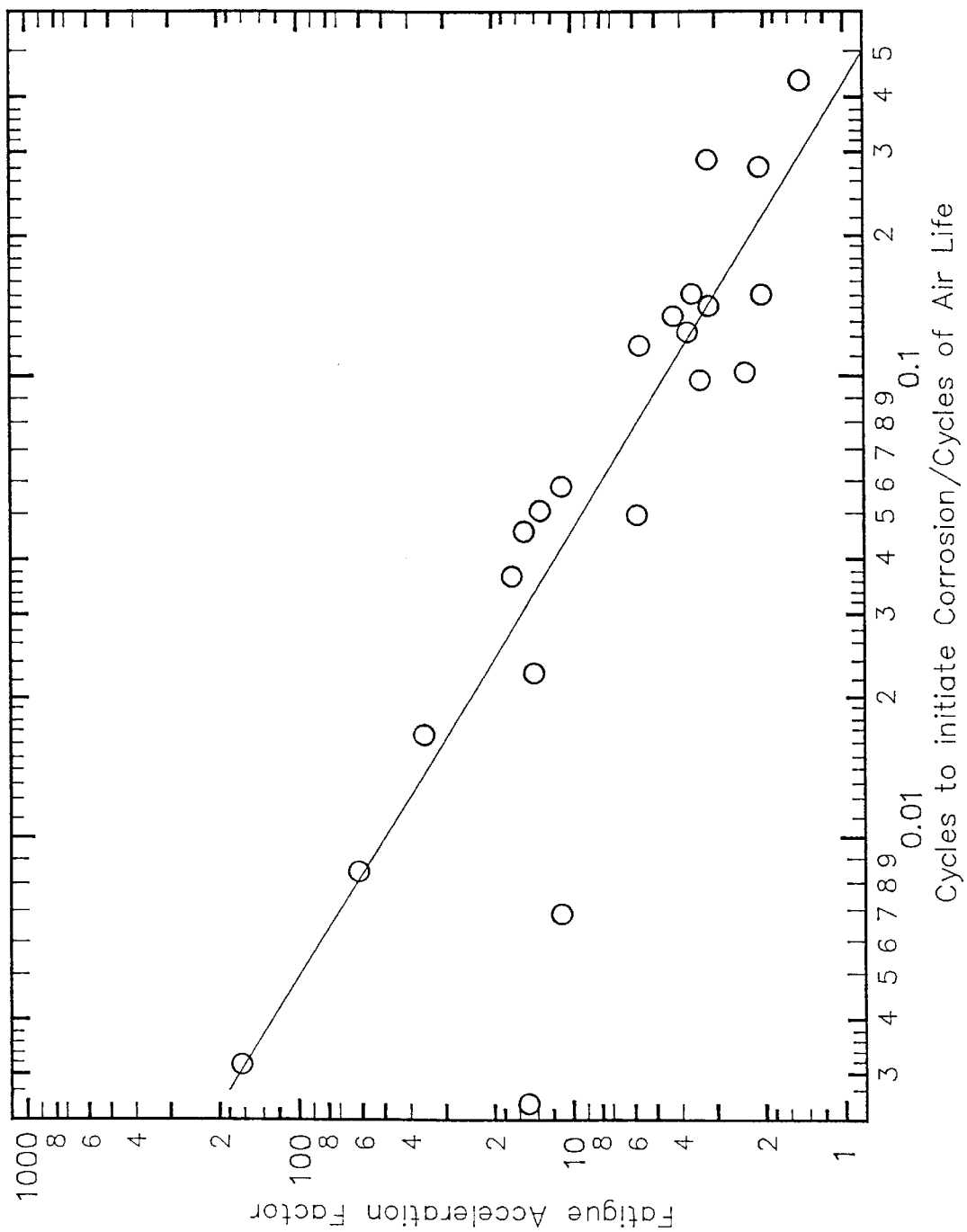
FIG. 15 shows the relationship between the number of cycles for acceleration of corrosion, the number of cycles to failure of the cable in air and the correlation with the acceleration factor for cable failure in the corrosive environment.

This minimization of the fundamental signal amplitude (magf0) can be seen in FIG. 14 which shows the fundamental (magf0) and the first two harmonics (magf1 and magf2) of the cyclic electrochemical potential response. The number of cycles (~82,500) where the minimum and change in phase occurs defines $N_c$, the number of cycles for acceleration of corrosion. This point represents the number of cycles after which the galvanically protective zinc coating has been removed by the corrosion fatigue or tribological process. The ratio, $N_c/N_o$, where $N_o$ is the number of cycles to failure of the cable in air, predicts the acceleration factor for cable failure in the corrosive environment, $N_o/N_{cor}$, where $N_{cor}$ is the number of cycles to failure for the cable in the corrosive environment. This correlation appears in FIG. 15.

These data confirm that localized corrosion is connected to fatigue damage of galvanized cable. Furthermore there appears to be an induction time for the onset of fatigue induced localized corrosion. The induction time is significantly less than the cable life. The analysis of signal phase indicates that the induction time corresponds to the lifetime of the galvanically protective zinc coating. This lifetime depends on the relative efficacy of the cable lubricant in inhibiting corrosion. The corresponding induction time, expressed in number of cycles Nc, provides an important metric for characterizing corrosion fatigue resistance of galvanized cable without corrosion-fatigue testing to failure.

In a further aspect, the present invention relates to a method of treating cable to be subjected to fatigue and the cable so treated. As in the case of the above described experiments, a length of cable in a given application will often have portions which experience fatigue, such as bending around pulleys, wheels, capstans, and the like, and portions which do not experience fatigue. Accordingly, rather than treating entire lengths or runs of cables, a cost savings benefit may be realized by identifying the portion or portions of the cable which will undergo fatigue, or at least the portion or portions undergoing the highest fatigue, in a given application and selectively applying additional corrosion protection thereto, while not treating the regions which do not undergo fatigue, or which at least do not undergo some minimum threshold level of fatigue, thus increasing cable life without the need to treat entire runs of material. The corrosion protection in the high fatigue and high wear regions of the cable may be accomplished by selective application of a corrosion protectant, such as additional grease or lubricant, corrosion inhibitors, passivating agents, or combinations thereof, to those regions which will undergo fatigue in a given application, without substantially applying such additional corrosion protection to the nonfatigue regions. Although the present invention employs the selective application of corrosion protection to the fatigue regions of a cable, it will be recognized that the present invention does not require that corrosion protectants be substantially absent in the nonfatigue regions and, in fact, the entire length of cable will generally have a lubricant, corrosion inhibitor, passivating agent, or the like thereon. For example, cables are typically received from the vendor with a lubricant or corrosion inhibitor thereon. The present invention relates to any additional protection selectively applied to only or substantially only the fatigue regions of a cable. Such protection is preferably applied in a manner or formulation that will be released over time.

The selective corrosion resistance may be accomplished by a number of methods. A first method is simply the initial application of a protecting agent, such as a lubricant and/or inhibitor formulation, to the high fatigue or high wear region or regions. Such formulations may be of the gel type or other type having good adherence. Another method of providing corrosion resistance in selected regions of the cable is to provide a reservoir from which a lubricant or inhibitor may be continuously be applied. In a preferred embodiment, pulleys containing timed-release corrosion inhibitors may be employed to maintain corrosion resistance in critical regions of the cable.

Figure 16:
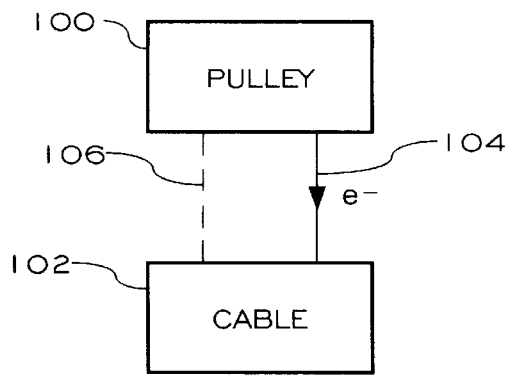
FIG. 16 is a block diagram illustrating an apparatus and method for inhibiting cable corrosion wherein a pulley which comprises a more active metal than the cable may be employed to provide cathodic protection to the cable.

Another method of providing corrosion resistance to the cable is to provide a pulley comprising a metal that has a more negative (active) potential in the corrosive medium or environment than the steel cable to be protected, as illustrated in FIG. 16. FIG. 16 depicts pulley 100 which is in contact with cable 102. By selecting a metal or an alloy thereof which is more active than the cable 102, pulley 100 will serve as an anode to provide cathodic protection to cable 102. In selecting a metal to fabricate or otherwise incorporate into pulley 100, the standard reversible single electrode potentials may serve as a guideline to select candidate metals, however, it will be recognized that they do not necessarily indicate whether a metal will be galvanically active with respect to the metal of the cable, such as steel, in a particular environment in which the cable may used. As such, the selection of a more active metal will depend on the environment in which the cable will be used. Exemplary metals which may be used in the pulley to provide cathodic protection to the cable include, for example, zinc, magnesium, cadmium, etc. It will be recognized that other metals may be employed as well, depending on the environment. For example, in some environments, tin may be usefully cathodically active with respect to steel. When the pulley 100 comprises a more active metal, pulley 100 and the cable 102 are in direct electrical connection as indicated by connection 104 by which the pulley 100 may supply its own electrons; preserving the cable. The circuit is completed by the electrolytic coupling indicated by dashed line 106 between the cable 102 (cathode) and pulley 100 (anode). This electrolytic coupling 106 may be through the corrodant in the environment, or, through a specially provided ionic conductor.

Figure 17:
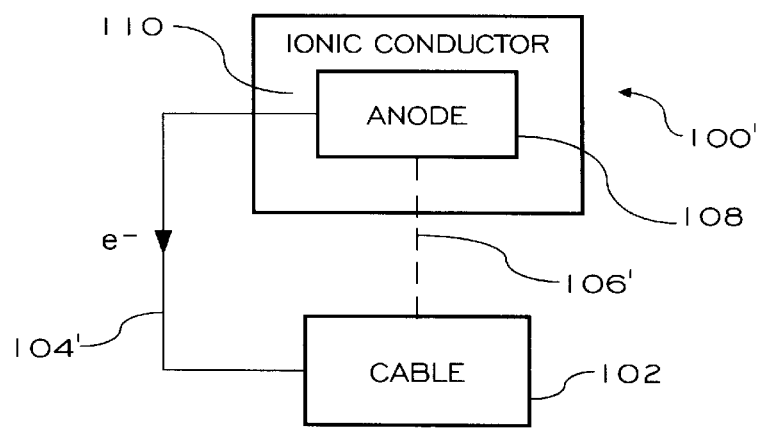
FIG. 17 is a block diagram illustrating an apparatus and method for inhibiting cable corrosion wherein a pulley that is directly electrically coupled to an anode comprising a more active metal than the cable may be employed to provide cathodic protection to the cable.

It will be recognized that it is not necessary for the entire pulley to be fashioned from the galvanically active metal. For example, as illustrated in FIG. 17, there is shown a pulley 100' comprising an internally located sacrificial anode 108 comprising a metal galvanically with respect to the cable 102 embedded in an ionically conducting and electronically nonconducting material 110 forming pulley. An external electrical contact 104' between embedded anode 108 and cable 102 is provided. The circuit is completed by an electrolytic (ionically conducting) connection 106' through material 110 between cable 102 and anode 108. It will be recognized that other configurations are possible as well. For example, in one embodiment, the anode 108 may be located externally of pulley 100' so long as the direct electrical connection 104' and the ionically conducting/electronically insulating connection 106' are maintained between cable 102 and anode 108. Any insulating material capable of transporting ions Materials useful as the electronic insulator/ionic conductor include, for example, porous polymers, ionic gels, porous ceramics, and the like.

Figure 18:
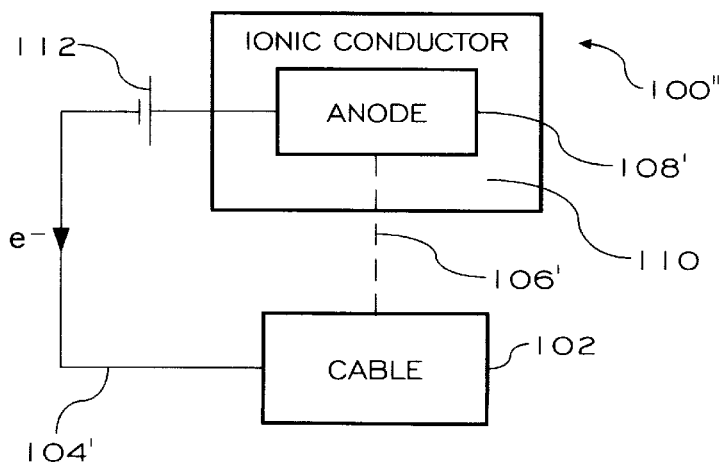
FIG. 18 is a block diagram illustrating an apparatus and method for inhibiting cable corrosion wherein cathodic protection is obtained from a direct current.

FIG. 18 illustrates another embodiment wherein an inert anode 108' embedded in an ionically conducting and electronically insulating material 110 forms a pulley 100". The anode 108' may be connected to a voltage source 112, such as a battery, and a direct electrical contact 104' is provided between anode 108' and cable 102. In this manner, the voltage source 112 may be employed to provide cathodic protection through an impressed current. An electronically insulating, ionically conducting coupling 106' is provided by the material 110 forming the pulley 100". In this manner, the negative terminal of the voltage source 112 will be connected to the cable. The positive terminal of the voltage source 112 is connected to the anode 108' which provides an electrolytic path between anode 108' and cable 102. The voltage source 112 may be located within the pulley 100", or, may be located externally of the pulley 100", with a direct electrical connection 104' to the cable. In one embodiment, the cable 102 may be employed, for example, in a vehicle having an electrical system, and the impressed current may be supplied by the vehicle's electrical system or power supply. It will be recognized that still other configurations are possible as well. For example, in one embodiment, the anode 108' may be located externally of pulley 100" so long as the both direct electrical connection 104' and the ionically conducting/electronically insulating connection 106' are maintained between cable 102 and anode 108'.

The description above should not be construed as limiting the scope of the invention, but as merely providing illustrations to some of the presently preferred embodiments of this invention. In light of the above description and examples, various other modifications and variations will now become apparent to those skilled in the art without departing from the spirit and scope of the present invention as defined by the appended claims. Accordingly, the scope of the invention should be determined solely by the appended claims and their legal equivalents.

What is claimed is:

1. An apparatus for detecting localized corrosion of a galvanized cable undergoing mechanical fatigue, said apparatus comprising:

(a) a weir cell containing an electrolyte solution, said weir cell comprising a reference electrode for detecting the potential between said reference electrode and said cable;

(b) one or more pulleys, wherein said weir cell and said one or more pulleys are arranged such that at least a portion of said cable that passes around at least one of said at least one pulley also passes through said weir cell; and (c) a motion control device for moving said cable around said at least one pulley and through said weir cell.

2. The apparatus according to claim 1 wherein said weir cell and said one or more pulleys are arranged such that at least a portion of said cable does not pass around any of said one or more pulleys, and wherein a portion of said cable that does not pass around any of said one or more pulleys passes through said weir cell.

3. The apparatus according to claim 2 wherein the cable is anchored at one end and has a load attached to the other end.

4. The apparatus according to claim 3 wherein said motion control device is motorized.

5. The apparatus according to claim 4 wherein said motion control device is a linear drive stage operable to move said cable by controlling the motion of a moveable pulley.

6. The apparatus according to claim 1 wherein each end of said cable is attached to a moveable member.

7. The apparatus according to claim 1 wherein said electrolyte is corrosive.

8. The apparatus according to claim 7 wherein said electrolyte is NaCl.

9. The apparatus according to claim 8 wherein said electrolyte solution comprises 5% NaCl.

10. A method for detecting the electrochemical response of corrosion coupled to fatigue in a galvanized steel cable, said method comprising the steps of:

(a) providing a moveable cable under tension;

(b) passing said cable around one or more pulleys and through a weir cell, said weir cell comprising an electrolyte solution, said weir cell further comprising a reference electrode for measuring the potential between said reference electrode and said cable;

(c) cyclically moving said cable such that a portion of said cable passes around at least one of said at least one pulley and wherein said portion of said cable also through said weir cell;

(d) recording the potential between said electrode and said cable.

11. The method according to claim 10 wherein said weir cell and said one or more pulleys are arranged such that at least a portion of said cable does not pass around any of said one or more pulleys, and wherein a portion of said cable that does not pass around any of said one or more pulleys passes through said weir cell.

12. The method according to claim 11 wherein said cable is anchored at one end and is attached to a load at the other end.

13. The method according to claim 12 wherein said step of cyclically moving the cable is performed by a motorized motion control device.

14. The method according to claim 13 wherein said motion control device is a linear drive stage operable to move said cable by controlling the motion of a moveable pulley.

15. The method according to claim 10 wherein each end of said cable is attached to a moveable member.

16. The method according to claim 10 wherein said electrolyte is corrosive.

17. The method according to claim 16 wherein said electrolyte is NaCl.

18. The method according to claim 17 wherein said electrolyte solution comprises 5% NaCl.

19. A method for monitoring the electrochemical response of a galvanized steel cable undergoing fatigue in a corrosive environment, said method comprising the steps of:

(a) providing a moveable cable under tension;

(b) passing said cable around one or more pulleys and through a weir cell, said weir cell comprising an electrolyte solution, said weir cell further comprising a reference electrode for measuring the potential between said reference electrode and said cable;

(c) cyclically moving said cable such that a portion of said cable passes around at least one of said at least one pulleys and wherein said portion of said cable also through said weir cell;

(d) recording the potential between said electrode and said cable as a function of time to produce an electrical signal representative of a waveform;

(e) determining the frequency content of said waveform, said frequency content comprising a fundamental harmonic and higher harmonics;

(f) determining the magnitudes of said fundamental harmonic and/or said higher harmonics; and (g) recording the changes in the magnitudes of said fundamental harmonic and/or said higher harmonics, said changes in the magnitudes of said fundamental harmonic and/or said higher harmonics providing an indicia of a change in electrochemical response.

20. The method according to claim 19 wherein said weir cell and said one or more pulleys are arranged such that at least a portion of said cable does not pass around any of said one or more pulleys, and wherein a portion of said cable that does not pass around any of said one or more pulleys passes through said weir cell.

21. The method according to claim 20 wherein said cable is anchored at one end and is attached to a load at the other end.

22. The method according to claim 20 wherein said step of cyclically moving the cable is performed by a motion control device operable to move said cable by controlling the motion of a moveable pulley.

23. The method according to claim 19 wherein each end of said cable is attached to a moveable member.

24. The method according to claim 19 wherein said electrolyte is NaCl.

* * * * *